US008449445B2

(12) United States Patent
Ludlow et al.

(10) Patent No.: US 8,449,445 B2
(45) Date of Patent: May 28, 2013

(54) DEVICE FOR VOLITIONAL SWALLOWING WITH A SUBSTITUTE SENSORY SYSTEM

(75) Inventors: Christy Leslie Ludlow, Bethesda, MD (US); Newlin Morgan, Bethesda, MD (US); George Dold, Boyds, MD (US); Soren Lowell, Syracuse, NY (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 992 days.

(21) Appl. No.: 12/240,398

(22) Filed: Sep. 29, 2008

(65) Prior Publication Data

US 2009/0054980 A1 Feb. 26, 2009

Related U.S. Application Data

(63) Continuation of application No. PCT/US2007/007993, filed on Mar. 30, 2007.

(60) Provisional application No. 60/787,215, filed on Mar. 30, 2006.

(51) Int. Cl.
*A61H 1/00* (2006.01)

(52) U.S. Cl.
USPC .............................. 600/23; 623/9

(58) Field of Classification Search
USPC ............ 600/23, 24, 25; 607/45, 72; 623/9
See application file for complete search history.

(56) References Cited

U.S. PATENT DOCUMENTS

| 4,143,648 | A | * | 3/1979 | Cohen et al. | 600/23 |
| 4,685,448 | A | * | 8/1987 | Shames et al. | 600/23 |
| 5,086,788 | A | * | 2/1992 | Castel et al. | 607/150 |

(Continued)

FOREIGN PATENT DOCUMENTS

| CN | 101716394 | 6/2010 |
| EP | 0 226 333 A1 | 6/1987 |

(Continued)

OTHER PUBLICATIONS

Extended European Search Report for European Patent Application No. 11005014.3 dated Sep. 30, 2011.

(Continued)

*Primary Examiner* — Charles A Marmor, II
*Assistant Examiner* — Joshua D Lannu
(74) *Attorney, Agent, or Firm* — Knobbe Martens Olson & Bear LLP

(57) ABSTRACT

A device for volitional swallowing with a substitute sensory system comprises a band 101 wrapped around the neck with a vibrator 102 positioned over the larynx. Upon activation by a button 103 on a spoon 104 held by an operator, such as the subject 105, the vibrator 102 moves and vibrates the larynx. The patient 105 initiates the sensory stimulation immediately prior to the patient's own initiation of a swallow by viewing on a display screen 106 a movement feedback signal 107, possibly from a piezo-electric sensor 108 also contained in the band 101 which will also be displayed on the display screen 106. The signal 109 from the switch device initiating sensory stimulation will be presented on the same display screen 106 for the patient 105 and trainer to observe when the button or switch 103 is activated for sensory stimulation in relation to the onset of the swallow.

41 Claims, 7 Drawing Sheets

U.S. PATENT DOCUMENTS

| | | | |
|---|---|---|---|
| 5,111,814 A | 5/1992 | Goldfarb | |
| 5,350,407 A * | 9/1994 | McClure et al. | 607/16 |
| 5,562,718 A | 10/1996 | Palermo | |
| 5,725,564 A | 3/1998 | Freed et al. | |
| 5,871,508 A | 2/1999 | Thompson et al. | |
| 5,891,185 A * | 4/1999 | Freed et al. | 607/72 |
| 5,897,579 A | 4/1999 | Sanders | |
| 5,987,359 A | 11/1999 | Freed et al. | |
| 6,039,679 A | 3/2000 | Yu | |
| 6,104,958 A | 8/2000 | Freed et al. | |
| 6,131,535 A | 10/2000 | So | |
| 6,198,970 B1 | 3/2001 | Freed et al. | |
| 6,343,232 B1 | 1/2002 | Mower | |
| 6,354,991 B1 | 3/2002 | Gross et al. | |
| 6,393,323 B1 | 5/2002 | Sawan et al. | |
| 6,735,315 B1 | 5/2004 | Ifukube et al. | |
| 7,039,468 B2 | 5/2006 | Freed et al. | |
| 7,182,738 B2 | 2/2007 | Bonutti et al. | |
| 7,280,873 B2 | 10/2007 | Freed et al. | |
| 7,349,739 B2 | 3/2008 | Harry et al. | |
| 7,606,623 B2 | 10/2009 | Ludlow et al. | |
| 7,660,636 B2 | 2/2010 | Castel et al. | |
| 2002/0010495 A1 | 1/2002 | Freed et al. | |
| 2002/0049479 A1 | 4/2002 | Pitts | |
| 2002/0133194 A1 | 9/2002 | Leelamanit et al. | |
| 2003/0093128 A1 | 5/2003 | Freed et al. | |
| 2004/0073271 A1 | 4/2004 | Harry et al. | |
| 2004/0133133 A1 | 7/2004 | Dreimann et al. | |
| 2005/0049453 A1 * | 3/2005 | Faulkner | 600/38 |
| 2005/0049856 A1 | 3/2005 | Baraff | |
| 2005/0059909 A1 | 3/2005 | Burgess | |
| 2006/0030794 A1 | 2/2006 | Nation et al. | |
| 2007/0073361 A1 | 3/2007 | Goren et al. | |
| 2007/0293926 A1 | 12/2007 | Dunlay et al. | |
| 2008/0077192 A1 | 3/2008 | Harry et al. | |
| 2009/0048645 A1 | 2/2009 | Philipp et al. | |
| 2009/0187124 A1 | 7/2009 | Ludlow et al. | |
| 2010/0016908 A1 | 1/2010 | Martin et al. | |
| 2010/0049103 A1 | 2/2010 | Ludlow et al. | |
| 2011/0125212 A1 | 5/2011 | Tyler | |
| 2012/0296243 A1 | 11/2012 | Ludlow et al. | |

FOREIGN PATENT DOCUMENTS

| | | |
|---|---|---|
| JP | 11-500339 | 1/1999 |
| JP | 2006-500994 | 1/2006 |
| JP | 2007-151736 | 6/2007 |
| WO | WO 92/21407 | 12/1992 |
| WO | WO 97/15349 | 5/1997 |
| WO | WO 2004/028433 A2 | 4/2004 |
| WO | WO 2007/005582 | 1/2007 |
| WO | WO 2010/033594 | 3/2010 |

OTHER PUBLICATIONS

Aviv et al., "Laryngopharyngeal sensory testing with modified barium swallow as predictors of aspiration pneumonia after stroke", *Laryngoscope*, 107:1254-1260 (1997).

Aviv et al., "Silent laryngopharyngeal sensory deficits after stroke", *Ann Otol Rhinol. Laryngol.*, 106:87-93 (1997).

Aviv et al., "Supraglottic and pharyngeal sensory abnormalities in stroke patients with dysphagia", *Ann Otol Rhinol.Laryngol.*, 105:92-97 (1996).

Bara-Jimenez et al., "Abnormal somatosensory homunculus in dystonia of the hand", *Ann Neurol.*, 44(5):828-831 (1998).

Bara-Jimenez et al., "Sensory discrimination capabilities in patients with focal hand dystonia", *Ann Neurol.*, 47(3):377-380 (2000).

Bidus et al., "Effects of Adductor Muscle Stimulation on Speech in Abductor Spasmodic Cysphonia", *The Laryngoscope*, 110:1943-1949 (2000).

Bielamowicz et al., "Effects of botulinum toxin on pathophysiology in spasmodic dysphonia", *Ann Otol Rhinol Laryngol*, 109:194-203 (2000).

Burnett et al., "Laryngeal elevation achieved by neuromuscular stimulation at rest", *J Appl Physiol*, 94(1):128-134 (2003).

Burnett et al., "Self-Triggered Functional Electrical Stimulation During Swallowing", *J Neurophysiol*, 94(6):4011-4018 (2005).

Conforto et al. "Increase in hand muscle strength of stroke patients after somatosensory stimulation", *Ann Neurol*, 51(I):122-125 (2002).

Supplementary European Search Report dated May 14, 2008.

Daly et al., "Performance of an intramuscular electrode during functional neuromuscular stimulation for gait training post stroke", *Journal of Rehabilitation Research and Development*, 38(5):513-526 (2001).

de Larminat et al., "Alteration in swallowing reflex after extubation in intensive care unit patients", *Crit Care Med*, 23(3):486-490 (1995).

De Nil et al., "Kinaesthetic acuity of stutterers and non-stutterers for oral and non-oral movements", *Brain*, 114:2145-2158 (1991).

Dick et al., "Interaction between central pattern generators for breathing and swallowing in the cat", *J Physiol*, 465:715-730 (1993).

Folstein et al., "Mini-mental state. A practical method for grading the cognitive state of patients for the clinician", *J Psychiatr Res*, 12(3):189-198 (1975).

Fraser et al., "Differential changes in human pharyngoesophageal motor excitability induced by swallowing, pharyngeal stimulation, and anesthesia", *Am J Physiol Gastrointest Liver Physiol*, 285(1):G137-144 (2003).

Freed et al., "Electrical Stimulation for Swallowing Disorders Caused by Stroke", *Respiratory Care*, 46(5):466-474 (2001).

Hägg et al., "Effects of motor and sensory stimulation in stroke patients with long-lasting dysphagia", *Dysphagia*, 19:219-230 (2004).

Hamdy et al., "Modulation of human swallowing behaviour by thermal and chemical stimulation in health and after brain injury", *Neurogastroenterol Motil*, 15(1):69-77 (2003).

Handa et al., "Development of Percutaneous Intramuscular Electrode for Multichannel FES System", *IEEE Transactions on Biomedical Engineering*, 36(7):705-710.

Haslinger et al., "Silent event-related fMRI reveals reduced sensorimotor activation in laryngeal dystonia", *Neurology*, 65:1562-1569 (2005).

Hrycyshyn et al., "Electromyography of the Oral Stage of Swallowing in Man", *Am. J. Anat.*, 133:333-340 (1972).

Humbert et al., "The effect of surface electrical stimulation on hyolaryngeal movement in normal individuals at rest and during swallowing", *J Appl Physiol*, 101:1657-1663 (2006).

Humbert et al., "The Effect of Surface Electrical Stimulation on Vocal Fold Position", *Laryngoscope*, 118:14-19 (2007).

International Search Report dated Apr. 9, 2004 (PCT/US03/30032).

International Search Report dated Nov. 21, 2006 (PCT/US2006/025535).

Jafari et al., "Sensory regulation of swallowing and airway protection: a role for the internal superior laryngeal nerve in humans", *J Physiol*, 550(Pt I):287-304 (2003).

Jean, "Control of the central swallowing program by inputs from the peripheral receptors. A review", *J Auton. Ner. Syst.*, 10:225-233 (1984).

Leelamanit et al., "Synchronized electrical stimulation in treating pharyngeal dysphagia", *Laryngoscope*, 112(12):2204-2210 (2002).

Logemann et al., "Effects of a sour bolus on oropharyngeal swallowing measures in patients with neurogenic dysphagia", *J Speech Hear Res*, 38(3):556-563 (1995).

Logemann, "Noninvasive approaches to deglutitive aspiration", *Dysphagia*, 8(4):331-333 (1993).

Loucks et al., "Laryngeal muscle responses to mechanical displacement of the thyroid cartilage in humans", *J Appl Physiol*, 99(3):922-930 (2005).

Lowell et al., "Sensory stimulation activates both motor and sensory components of the swallowing system", *NeuroImage*, 42:285-295 (2008).

Ludlow et al., "Chronic Intermittent Stimulation of the Thyroarytenoid Muscle Maintains Dynamic Control of Glottal Adduction", *Muscle and Nerve*, 23:44-57 (2000).

Ludlow et al., "Dynamic aspects of phonatory control in spasmodic dysphonia", *J Speech Hear Res*, 30:197-206 (1987).

Ludlow et al., "Effects of Surface Electrical Stimulation Both at Rest and During Swallowing in Chronic Pharyngeal Dysphagia", *Dysphagia*, 22:1-10 (2007).

Ludlow et al., "Three-Dimensional Changes in the Upper Airway During Neuromuscular Stimulation of Laryngeal Muscles", *Journal of Artificial Organs*, 23:463-465 (1999).

Lundy et al., "Aspiration: Cause and Implications", *Otolaryngol Head Neck Surg.*, 120(4):474-478 (1999).

Marsolais et al., "Implantation techniques and experience with percutaneous intramuscular electrodes in the lower extremities", *J. Rehabil. Res. Dev.*, 23(3):1-8 (1986).

Mifflin, "Intensity and frequency dependence of laryngeal afferent inputs to respiratory hypoglossal motoneurons", *J Appl Physiol*, 83:1890-1899 (1997).

Mortimer et al., "Intramuscular Electrical Stimulation: Tissue Damage", *Ann. Biomed. Eng.*, 8:235-244 (1980).

Nishino et al. (1996). Cough and other reflexes on irritation of airway mucosa in man. Pulm Pharmacol, 9(5-6):285-292 (1996).

Ootani et al., "Convergence of afferents from the SLN and GPN in cat medullary swallowing neurons", *Brain Res Bull*, 37(4):397-404 (1995).

Park et al., "A pilot exploratory study of oral electrical stimulation on swallow function following stroke: an innovative technique", *Dysphagia*, 12(3):161-166 (1997).

Peurala et al., "Cutaneous electrical stimulation may enhance sensorimotor recovery in chronic stroke", *Clin Rehabil.*, 16:709-716 (2002).

Pick et al., "Pulmonary aspiration in a long-term care setting: clinical and laboratory observations and an analysis of risk factors", *J Am Geriatr Soc*, 44(7):763-768 (1996).

Pommerenke, "A study of the sensory areas eliciting the swallowing reflex", *American Journal of Physiology*, 84(1):36-41 (1927).

Portone et al., "A review of patient adherence to the recommendations for voice therapy", *J. Voice*, 22:192-196 (2008).

Power et al., "Changes in pharyngeal corticobulbar excitability and swallowing behavior after oral stimulation", *Am J Physiol Gastrointest Liver Physiol*, 286(1):G45-50 (2004).

Power et al., "Evaluating oral stimulation as a treatment for Dysphagia after stroke", *Dysphagia*, 21(1):49-55 (2006).

Robbins et al., "Swallowing and dysphagia rehabilitation: translating principles of neural plasticity into clinically orientated evidence", *J Speech Lang. Hear. Res.*, 51:S276-300 (2008).

Scheiner et al., "Design and Clinical Application of a Double Helix Electrode for Functional Electrical Stimulation", *IEEE Transactions of Biomedical Engineering*, 41(5):425-431 (1994).

Sedory-Holzer et al., "The swallowing side effects of botulinum toxin type A injection in spasmodic dysphonia", *Laryngoscope*, 106:86-92 (1996).

Setzen et al., "The association between laryngopharyngeal sensory deficits, pharyngeal motor function, and the prevalence of aspiration with thin liquids", *Otolaryngol Head Neck Surg*, 128(1):99-102 (2003).

Spiro et al., "Activation and Coordination Patterns of the Suprahyoid Muscles During Swallowing", *Laryngoscope*, 104:1376-1382 (1994).

Stanic et al., "Multichannel Electrical Stimulation for Correction of Hemiplegic Gait", *Scand J. Rehabil. Med.*, 10:75-92 (1978).

Strojnik et al., "Treatment of Drop Foot Using an Implantable Peroneal Underknee Stimulator", *Scand J. Rehabil. Med.*, 19:37-43 (1987).

Struppler et al., "Modulation of sensorimotor performances and cognition abilities induced by RPMS: clinical and experimental investigations", *Suppl Clin Neurophysiol.*, 56:358-367 (2003).

Sundgren et al., "Elevation of the larynx on normal and abnormal cineradiogram", *The British Journal of Radiology*, 66:768-772 (1993).

Theurer et al., "Oropharyngeal stimulation with air-pulse trains increases swallowing frequency in healthy adults", *Dysphagia*, 20(4):254-260 (2005).

van Dijk et al., "Effects of transcutaneous electrical nerve stimulation (TENS) on non-pain related cognitive and behavioural functioning", *Rev Neurosci.*, 13:257-270 (2002).

Waters et al., "Functional Electrical Stimulation of the Peroneal Nerve for Hemiplegia", *The Journal of Bone and Joint Surgery*, 67:792-793 (1985).

International Search Report and Written Opinion of the International Searching Authority for International Application No. PCT/US2006/025535, mailed on Nov. 21, 2006.

International Preliminary Report on Patentability and Written Opinion of the International Searching Authority for International Application No. PCT/US2006/025535, issued on Jan. 9, 2008.

International Search Report and Written Opinion of the International Searching Authority for International Application No. PCT/US2007/007993, mailed on Mar. 5, 2008.

International Preliminary Report on Patentability and Written Opinion of the International Searching Authority for International Application No. PCT/US2007/007993, issued on Sep. 30, 2008.

International Search Report for International Application No. PCT/US2009/057158, mailed on Mar. 26, 2010.

International Preliminary Report on Patentability and Written Opinion of the International Searching Authority for International Application No. PCT/US2009/057158, issued on Mar. 22, 2011.

Office Action issued in Australian Patent Application No. 2006265985 on Oct. 20, 2009.

Notice of Acceptance issued in Australian Patent Application No. 2006265985 on Dec. 1, 2010.

Office Action issued in European Patent Application No. 06785933.0 on Feb. 10, 2011.

Office Action issued in Japanese Patent Application No. 2008-520302 on Nov. 15, 2011.

Final Office Action in Japanese Application No. 2008-520302, dated Aug. 14, 2012.

Final Office Action issued in U.S. Appl. No. 11/993,094, dated Oct. 16, 2012.

Final Office Action issued in U.S. Appl. No. 12/211,633, dated Sep. 17, 2012.

First Action Interview Pilot Program Pre-Interview Communication issued in U.S. Appl. No. 13/492,044, dated Oct. 18, 2012.

Notice of Allowance issued in U.S. Appl. No. 12/211,633, dated Oct. 30, 2012.

Office Action in Australian Patent Application No. 2011201177, dated Aug. 1, 2012.

Office Action issued in EP Application No. 11 005 014.3, dated Jun. 8, 2012.

Restriction Requirement issued in U.S. Appl. No. 11/993,094 on Jan. 24, 2012.

Andersen et al., Modulation of heat evoked nociceptive withdrawal reflexes by painful intramuscular conditioning stimulation, *Exp Brain Res*, 2006, vol. 174, pp. 755-780.

Bhadra et al., Extraction Force and Tissue Change During Removal of a Tined Intramuscular Electrode from Rat Gastrocnemius, *Annals of Biomedical Engineering*, Jun. 2006, vol. 34, No. 6, pp. 1042-1050.

Caetano et al., Evidence of vibrotactile input to human auditory cortex, *NeuroImage*, 2006, vol. 29, pp. 15-28.

Celichowski et al., The time course of the last contractions during incompletely fused tetani of motor units in rat skeletal muscle, *Acta Neurobiol. Exp.*, 2002, vol. 62, pp. 7-17.

Chou et al., Predicting optimal electrical stimulation for repetitive human muscle activation, *Journal of Electromyography and Kinesiology*, 2005, vol. 15, pp. 300-309.

Davis et al., Quantitative analysis of laryngeal mechanosensitivity in the cat and rabbit, *J. Physiol.*, 1987, vol. 388, pp. 467-485.

Grottel et al., The Influence of changes in the stimulation pattern on force and fusion in motor units of the rat medial gastrocnemius muscle, *Exp Brain Res*, 1999, vol. 127, pp. 298-306.

Jean, Brain Stem Control of Swallowing: Neuronal Network and Cellular Mechanisms, *Physiological Reviews*, Apr. 2001, vol. 81, No. 2, pp. 929-969.

Kesar et al., Effect of frequency and pulse duration on human muscle fatigue during repetitive electrical stimulation, *Exp Physiol*, 2006, vol. 91, No. 6, pp. 967-976.

Kitagawa et al., Facilitation of reflex swallowing from the pharynx and larynx, *Journal of Oral Science*, 2009, vol. 51, No. 2, pp. 167-171.

Knutson et al., Electrode fracture rates and occurrences of infection and granuloma associated with percutaneous intramuscular electrodes in upper-limb functional electrical stimulation applications, *Journal of Rehabilitation Research and Development*, 2002, vol. 39, Issue No. 6, pp. 671-683.

Mortimer et al., Vibrotactile transduction and transducers, *J. Acoust. Soc. Am.*, May 2007, vol. 121, No. 5, pp. 2970-2977.

Pertovaara, Modification of human pain threshold by specific tactile receptors, *Acta Physiol Scand*, 1979, vol. 107, pp. 339-341.

Wakeling et al., Muscle activity damps the soft tissue resonance that occurs in response to pulsed and continuous vibrations, *J Appl Physiol*, May 17, 2002, vol. 93, pp. 1093-1103.

Witteveen et al., Vibro- and Electrotactile User Feedback on Hand Opening for Myoelectric Forearm Prostheses, *IEEE Transactions on Biomedical Engineering*, Aug. 2012, vol. 59, No. 8, pp. 2219-2226.

Experia™: The Next Generation of VitalStim® Therapy brochure, 2007 Encore Medical, L.P. and Affiliates, 2 pages.

Office Action issued in Australian Patent Application No. 2011201177, dated Feb. 23, 2012.

Office Action issued in U.S. Appl. No. 11/993,094, dated Mar. 13, 2012.

Office Action issued in U.S. Appl. No. 12/211,633, dated Jan. 4, 2012.

* cited by examiner

DEVICE FOR VOLITIONAL SWALLOWING WITH A SUBSTITUTE SENSORY SYSTEM

CROSS REFERENCE TO RELATED APPLICATION

This application is a continuation under 37 CFR §1.53(b) and 35 U.S.C. §111(a) of pending prior international application Number PCT/US2007/007993, filed Mar. 30, 2007, and claims priority to U.S. Provisional Patent Application Ser. No. 60/787,215, filed Mar. 30, 2006, the disclosure of which are incorporated herein by reference.

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

BACKGROUND OF THE INVENTION

1. Field of the Invention

The invention relates generally to methods and devices for treating neurological diseases and disorders affecting swallowing. The invention provides for the patient and the trainer of the patient to control the timing of switching stimulation to control a swallow at the optimal time when the patient desires to swallow.

2. Description of the Related Art

A wide range of neurological diseases and disorders exist that are not well addressed by present medical technology. Among these, dysphagia is a disorder placing persons at risk of aspiration pneumonia, a life-threatening condition. Subjects at risk of aspiration pneumonia have a 17% survival rate over three years. Estimates are that over 3 million persons in the U.S. have dysphagia as a result of neurological diseases or disorders such as stroke, traumatic brain injury, brain tumors, Parkinson's disease, multiple sclerosis and other neurological diseases and over 300,000 persons develop a swallowing disorder as a result of a neurological disease or disorder in the United States each year. Over 50% of subjects with neurological diseases or disorders are at risk of aspiration pneumonia because of loss of central nervous system control of their swallowing resulting in either delayed or reduced elevation of the hyolaryngeal complex, which does not allow them to prevent food or liquid from entering the airway. Normally the hyoid and larynx are raised by about 20 mm during swallowing producing an inversion of the epiglottis and assisting with opening of the upper esophageal sphincter. Many therapeutic techniques aim to improve hyolaryngeal elevation and reduce aspiration risk in dysphagia.

Many other disorders need treatment, particularly as a result of stroke and other neurological diseases. In addressing these treatment needs, research has demonstrated that somatosensory stimulation can potentiate recovery of hand movement post stroke.

Others have shown that somatosensory stimulation applied to a paretic hand has transient beneficial effects on the paretic hand pinch force in patients with stroke. It has previously been shown that electrical, heat or a bolus in the hypopharynx can trigger swallowing while laryngeal sensory blocks will severely impair the initiation of volitional swallowing in normal adults. Pharyngeal stimulation can initiate laryngeal closure and elevation for swallowing in animals, while laryngeal stimulation will trigger a swallow. In humans, when sensory stimulation of the oropharynx is presented during a period separate from swallowing, it enhances cortical activity in the swallowing regions, but does not benefit subsequent swallowing in dysphagic subjects. Thus, further discoveries are needed in this area.

Broad methods and devices are presented for therapy of neuromuscular disorders such as dysphagia. By training subjects afflicted with dysphagia to coordinate their own swallowing with intramuscular stimulation, their central volitional control was found to also improve, without stimulation after training. Subjects could improve quickly in their ability to trigger stimulation at the same time as intended swallow. Results indicate that normal persons can easily and spontaneously coordinate the onset of a button press with the onset of muscle activation for the pharyngeal component of swallowing. Accordingly, subjects with dysphagia can learn to coordinate a muscular movement such as a button press with swallowing onset. In other embodiments, other muscle movements similarly are quickly learned in a similar manner.

Therefore, there is need for device to permit the patient to coordinate muscular movement with a button press to permit volitional swallowing.

SUMMARY OF THE INVENTION

These and other needs are addressed by the present invention, in which a device is provided for allowing the subject with dysphagia to coordinate muscular movement with a button press to permit volitional swallowing.

In one aspect of the present invention, a device for treating a subject with dysphagia or a speech disorder is disclosed. It comprises a connector for attaching the device to the patient's neck, substantially over the subject's larynx. The device also comprises a contact section for contacting the subject's neck above the larynx. Additionally, the device also comprises a stimulator for applying at least one stimulus to the subject's larynx. Also, the device comprises an adjustment mechanism for shifting the position of the device over the subject's larynx.

In another aspect of the present invention, a device for enhancing volitional control of a subject's larynx is disclosed. The device comprises a movement sensor for monitoring pressure or movement changes due to elevation of the subject's larynx during attempts to swallow, serving as a swallowing detector. The swallowing detector further comprises a piezoelectric deflection receptor or a pressure sensor. It also comprises a stimulator, coupled to the movement sensor, for applying pressure to a subject's larynx prior to swallowing. The swallowing detector additionally comprises a battery, contained within the stimulator, acting as a power supply for the device. The swallowing detector also comprises one or more physiological sensors, electrically coupled to the stimulator. The device next comprises a control device, a button either alone or contained in a spoon handle. The control device further comprises a transducer, activated by the subject, for sending a signal to the stimulator before the subject attempts to swallow or speak. It also comprises a control box for selecting the stimulus type, rate and amplitude. The control box also comprises a cover, for protecting the device when not in use by the subject.

In yet another aspect of the present invention, a vibro-tactile stimulator for providing subject-controlled stimulation to the larynx is disclosed. The vibro-tactile stimulator comprises a digital clock generator for producing an initial clock signal having a first frequency range. It also comprises a digital decade counter for receiving the initial clock signal and for producing sequential pulses having a second frequency range. Additionally, the vibro-tactile stimulator comprises a motor, responsive to the sequential pulses, for producing vibrations on the subject's larynx, having a third frequency range.

In still another aspect of the present invention, an automatic stimulation controller device that cycles on and off to initiate and maintain vibro-tactile stimulation to induce swallowing during the day and/or night to provide saliva control by swallowing is disclosed. The automatic stimulation controller device comprises an automatic clock that initiates the onset of the device. It also comprises an adjustable clock to initiate stimulation at an adjustable interval of between about 1 and about 5 minutes. Additionally, the automatic stimulation controller device comprises an adjustable timer that allows for setting the duration of stimulation between about 1 and about 10 seconds. The automatic stimulation controller device can also be adjusted to different intervals and durations of stimulation. It can additionally be adjusted to stimulation rates of between about 30 and about 70 Hz of vibro-tactile stimulation.

Other aspects, features, and advantages of the present invention are readily apparent from the following detailed description. The present invention is also capable of other and different embodiments, and its several details can be adjusted without departing from the scope of the invention. Thus, the drawings and description are illustrative and not restrictive.

DETAILED DESCRIPTION OF THE PREFERRED EMBODIMENTS

It was discovered that neurologically impaired patients with dysphagia could improve voluntary initiation of swallowing and thus alleviate their risk of aspiration while swallowing, by motor act habituation such as pressing a button to indicate when they feel ready to swallow. By way of example and not limitation, such motor training produces concurrent sensory stimulation that induces a central pattern that produces the related effect of swallowing. This principle is applicable to other neurological impairments, their associated motor act habitations and related sensory stimulations. Neurological impairments that are contemplated include reflex actions that involve interactions between afferent and efferent paths, at the spinal cord or in the brain stem, as well as higher order interactions.

Embodiments contemplated cover methods for treating neurologically impaired humans, devices useful for such treatments, such as those that produce deglutition stimulation and vocalization stimulation and/or combinations of these. Combinations of stimulation types are particular useful. Stimulation may be controlled electrically, mechanically, chemically or biologically. For example the combined use of button press training with simultaneous vibratory and pressure stimulation on the neck to augment feedback to the brain stem swallowing centers to facilitate voluntary control of swallowing, which is thought to be largely an involuntary brain stem function, is particularly useful for treating dysphagic subjects. That is, volitional training with simultaneous sensory stimulation can assist early rehabilitation of dysphagia.

A large variety of subjects may be treated with the devices and methods contemplated herein, including for example, humans and animals that have experienced any stroke, traumatic brain injury, post surgery to brain, Parkinsons, multiple sclerosis, ALS, supranuclear palsy or other neurological disease or injury.

The site for stimulation for each disease will be appreciated by a medical doctor or other allied health professional with experience with the disease. For dysphagia, stimulation over the larynx is contemplated. The stimulation site is to a substitute region for a sensory region that is normally able to elicit reflex swallowing but is no longer intact for a subject, resulting a suppression of reflex swallowing such as occurs following extubation. For example, subjects afflicted with dysphagia following neurological disease usually have sensory loss in the oropharyngeal area which is normally required to be sensate in order to elicit safe swallowing without aspiration in normal volunteers. Others have attempted providing stimulation to areas that are reduced in sensory function to enhance swallowing in subjects afflicted with dysphagia, and in normal volunteers; however these approaches to stimulation involve the placement of devices into the oral cavity which interferes with eating food and liquids.

Figure 7:
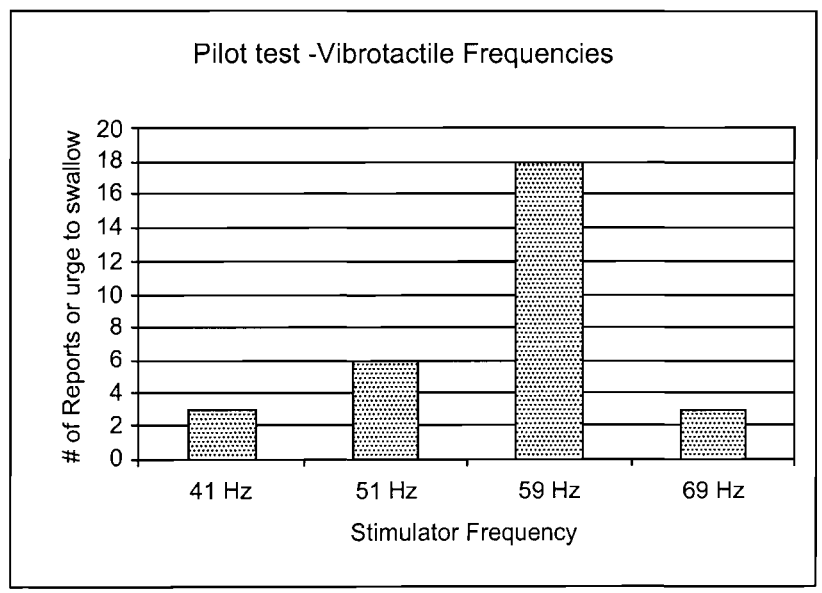
FIG. 7 is a histogram of the frequency of reports of urges to swallow when vibro-tactile stimulation at four different frequencies were presented to the throat area. The majority of the reports demonstrated that a rate of 59 Hz produced the most frequent reports of urges to swallow.

This embodiment uses sensory triggering in substitute areas known to also enhance the elicitation of reflex swallowing such as stimulation of afferents from the laryngeal area contained in the superior laryngeal area. Basic studies suggest that the second order neurons excited by afferents in the superior laryngeal nerve are selectively excitable at particular frequencies and that stimulation around 30 Hz may be preferred for exciting the swallowing system in the brainstem. As shown in FIG. 7 vibratory stimulation to the skin over the throat at 59 Hz produces the most frequent reports of an urge to swallow. Subjects are often not responsive to stimulation in the oral and pharyngeal cavities but remain sensate to vibratory stimulation to the areas of the human head which include anatomical structures (e.g., muscles, nerves or connective tissue) that work in concert to effect deglutition. By providing sensory stimulation to sensate areas on the throat, substitute stimulation can be used to enhance the volitional elicitation of swallowing.

An embodiment treating dysphagia can be applied to treat other diseases. In an embodiment, a period of volitional training with an alternate substitute sensory stimulation (for example vibro-tactile stimulation to the throat area) is carried out wherein a patient activates a switch to begin both vibration and/or pressure on the neck over the region of the larynx immediately before and during a swallow while the patient attempts to swallow to potentiate the subject's volitional control of a swallow. In an embodiment the switch is activated between about 0 and about 5 seconds, about 10 milliseconds ("ms") and about 1.5 seconds, more preferably between about 50 ms and about 750 ms yet more preferably between about 100 ms and about 500 ms and even more preferably between about 200 ms and about 400 ms before the volitional attempt at movement.

A pressure applying device that attaches to the body by for example a hook-and-loop fastener, strap, rubber band, belt, bandage, garment, ace bandage, wire, string, piezoelectric band or film, and/or combination of these. Desirably the applying device includes a contact pressure builder such as a balloon, inflatable tube that inflates to a desired pressure or volume. The art of blood pressure monitors includes devices and methods that may be used. Preferably a neck wrap is used that positions the pressure applying device to the larynx and is adjustable via a hook-and-loop fastener. A small point such as an area as small as about 0.02 square centimeter over the larynx may be pressed, although larger areas of from about 01. to about 10 $cm^2$, from about 0.25. to about 5 $cm^2$, from about 0.5 to about 2.5 $cm^2$ areas may be used. A desirable area is about a 2-cm diameter circle. In a desirable embodiment at least 25%, 35%, 50%, 75%, 85%, 90%, 98% or more of the total pressure (calculated as an integrated sum measurement of pressure times surface area) is placed over the larynx cartilage but not over surrounding muscle. In an embodiment, such selective pressure is achieved, to obtain satisfactory results. In another embodiment, vibratory energy similarly is selectively confined over the larynx versus the surrounding muscle. Desirably, less than 50%, 25%, 10%, 5% or even less pressure (and or stimulation such as cold, vibration, heat, electrical stimulation) is applied to neck muscles.

For restoration of neurologically impaired deglutition, a vibrator may be contacted over the larynx and produce a sequential wave of pressure across bars (such as 3 to 5 oblong bars) at about 0.5 to about 30 times per second, and more preferably 2 to 25 times, more preferably 5 to 10 times per second. Desirably the pressures are between about 1 to about 14 psi with rise times of about 25 to about 500 ms and more desirably rise times of about 75 to about 150 ms. The vibrator may be combined with another stimulator such as an electrical skin surface stimulator (same timing or different). Vibration rates of about 20 to about 100 Hz are preferred and between about 40 to about 60 (e.g. 50-60 Hz) most preferred. Amplitude of vibration desirably may be for example between about 1 micron and about 2 mm. Amplitudes between about 100 micron and about 1 mm are useful. Generally, electrical stimulation for sensory effects of the afferents in the skin most desirably include and more desirably employ biphasic pulses of between 1-5 milliamperes of current at 15 to 60 Hz as 50 and 200 microsecond pulses.

In a desirable embodiment applicable to all stimulation types (pressure, vibration, electrical, etc) the amplitude of the stimulation (measured as energy output or more directly as electrical current or vibration displacement etc) and/or the rate of the stimulation pulse increases during the swallowing activity. In another embodiment the duration of stimulation is set to the average measured, or expected duration of the subject's swallow. In an embodiment the stimulation lasts as long as the swallow is perceived to occur, or as long as a switch is activated.

In other embodiments, the stimulation device is covered by a disposable material such as a plastic or a cloth. Stimulators such as air pressure bars desirably (with vibrator and electrical stimulators if used, closest to the skin) may be contained within a stretchable device such as a wrap with a hook-and-loop fastener and is adjustable for individual subject bodies. In another embodiment the switch is a button or other electrical device that is covered when not in use. For example the switch may be a button in a small cover that is reversibly slid over the top of a spoon handle or spoon handle shaped mount.

Pressure and/or electrical stimulation desirably is applied at a frequency of between about 1 to about 100 Hz, about 5 to about 70 Hz, and more desirably between about 30-60 Hz. Electrical stimulation, if used should be at low levels of less than about 25 mA over a wide area (10 $cm^2$), or less if the area is smaller, such as between about 0.01 to about 10 mA, about 0.1 to about 7 mA, about 0.5 to about 5 mA, or about 1-3 mA. Levels that do not exceed about 10 mA, about 7 mA, about 5 mA, about 4 mA, about 3 mA, and more desirably about 2 mA, are particularly useful.

A study demonstrates improved swallowing safety (a reduction in aspiration) with the use of a low level electrical stimulation at about 2 mA in chronic dysphagic subjects. This study demonstrated that surface electrical stimulation at current intensities of about 7 mA or higher which will stimulate the neck muscles underlying the skin DO NOT benefit swallowing safety in dysphagic patients. Rather benefit occurred only when stimulation was at low levels that would only produce sensory stimulation to the skin but not at higher levels.

Less than about 70 Hz is particularly useful for sensory stimulation and can be combined with other stimuli. Less than about 60 Hz or less is particularly desirable for dysphagia and other disease states. About a 59 Hz stimulation is desirable in some low cost embodiments due to the easy availability of equipment for this frequency. Vibratory stimulation is envisioned as being much more rapid, being between about 10 and about 100 Hz and may be particularly useful at about 60 Hz.

Most desirably, the stimulation is asserted immediately before a volitional attempt to move or carry out the physiological impaired function, such as swallowing. In an embodiment, the stimulation is asserted about 1 to about 10 seconds before, about 0.1 to about 1 seconds before, about 0.2 seconds to about 0.5 seconds before or about 0.2 to about 0.4 seconds before the attempt. The stimulation may be asserted at the same time, but preferably is made, via a device held in place against the affected body part, beforehand by this prescribed time period. Other times and devices will be appreciated by a skilled worker (i.e. a biomedical engineer working with and informed by a neurophysiologist researcher).

Figure 1:
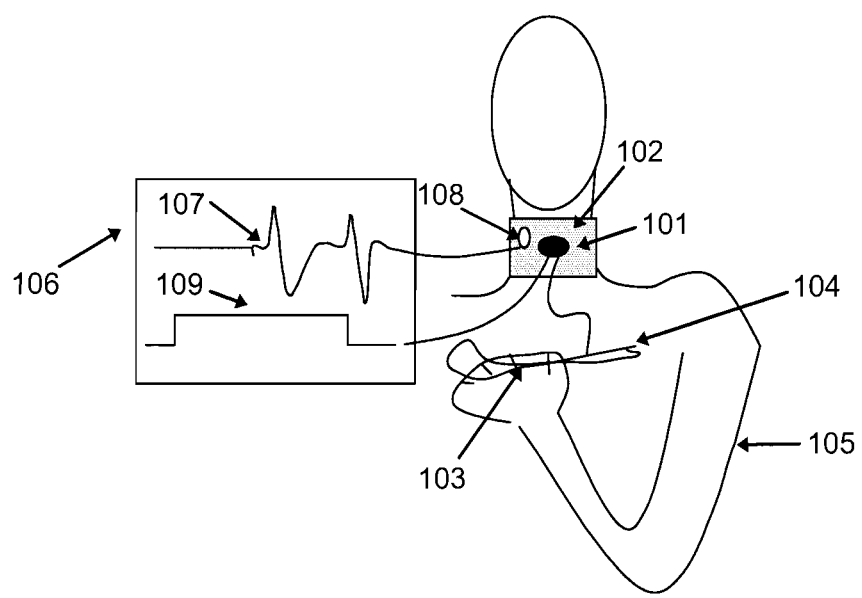
FIG. 1 is a diagram of a device for treating a subject afflicted with dysphagia or a speech disorder.

FIG. 1 depicts a device for treating dysphagia or a speech disorder. For dysphagia treatment, desirably a band 101 may be wrapped around the neck, with a vibrator 102 positioned over the larynx. Upon activation (e.g. by a button or switch 103) on a spoon 104 held by the subject 105 (one who wears the device, or under orders from the subject 105) the vibrator 102 moves and vibrates the larynx. A control box is contemplated that may be set to the stimulus type, the stimulus rate (set or increasing) and amplitude (set or increasing) parameters and whether the duration would be set or stay for about 2 to about 6 seconds or as long as the button is pressed.

In an embodiment, depicted in FIG. 1, instructions are provided to the subject 105 for practice of initiating the sensory stimulation immediately prior to the subject's 105 own initiation of a motor act such as swallowing by viewing, on a display screen 106, a movement feedback signal 107, possibly from a piezo-electric or pressure sensor 108 also contained in the neck wrap 101, which will be displayed when the motor movement begins on a display screen 106. The signal 109 from the switch 103, initiating sensory stimulation, will be presented on the same display screen 106 for the subject 105 and a trainer to observe when the button or switch 103 was activated for sensory stimulation in relation to the onset of the motor act or swallow. In this way the subject can learn to optimize the timing of the sensory switch to occur between about 600 and about 200 ms prior to the onset of their motor act of swallowing. Communication between the switch and the stimulator may be by telemetry rather than a wired device and similarly communication between the movement sensor and the display may be by telemetry to relieve the subject from wired devices.

Kits are contemplated that include at least one stimulating device that is adapted to be placed in contact with an affected body part, such as the larynx, a switch activated by a subject, instructions for use and a container for the device. The instructions desirably include at least one instruction corresponding to one or more method steps listed herein. In an embodiment, a power supply such as a battery is within the stimulating device. In an embodiment, disposable covers are included that cover the stimulator during use. In an embodiment the stimulating device includes at least one pump that increases pressure within a chamber such as balloon(s) or tube(s). The device further may include a pressure, stretch, volume, power or other sensor to monitor pressure exerted by the device. In an embodiment the device further includes a switch for setting the amount of desired pressure or movement and/or electrical stimulation. Switches also may exist for setting frequency and or amplitude of the stimulation. In another embodiment, the device in contact with the skin further includes one or more sensors of physiology, such as temperature, skin color, hematocrit, oxygenation, blood pressure and the like. In an embodiment the device reports results by a display and or by electromagnetic transmission. In an embodiment the device monitors and/or records swallowing events. For example, the device desirably monitors the presence (and optionally depth) of a swallowing event via a piezo electric stretch receptor or other sensor on or in the band around the neck, and/or at the surface over the larynx.

Changes and modifications to the embodiments presented herein are readily understood by the skilled artisan after reading this specification. In particular, each condition may be combined with other conditions stated herein.

Figure 2:
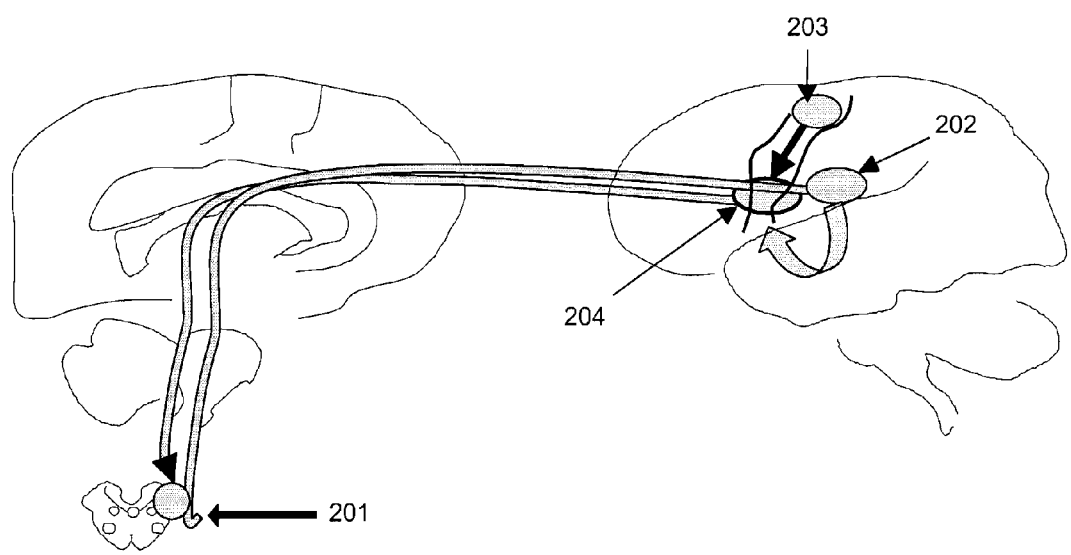
FIG. 2 is a diagram of neural circuitry involved in using hand control.

FIG. 2 illustrates the neural circuitry in using hand control 203 to trigger volitional swallowing 204 along with simultaneous sensory stimulation 201 which goes to the cortex 202. This is implemented after button press training described above with respect to FIG. 1. Elicitation of the swallowing reflex and safety in swallowing is dependent upon sensory feedback 201 to the brain from sensory mechanoreceptors in the upper airway. If sensory input is withdrawn, persons feel that they can no longer swallow and are at significant increase of aspiration during swallowing. The neural circuitry enhances cortical motor control 202 of swallowing coincident with substitution of sensory input 203 (from stimulation of the throat area) to trigger brain stem circuitry to trigger reflexive swallowing 204 simultaneous with volitional swallowing. Subjects with swallowing difficulties following stroke have often lost their ability to sense stimuli in the upper airway.

Figure 3:
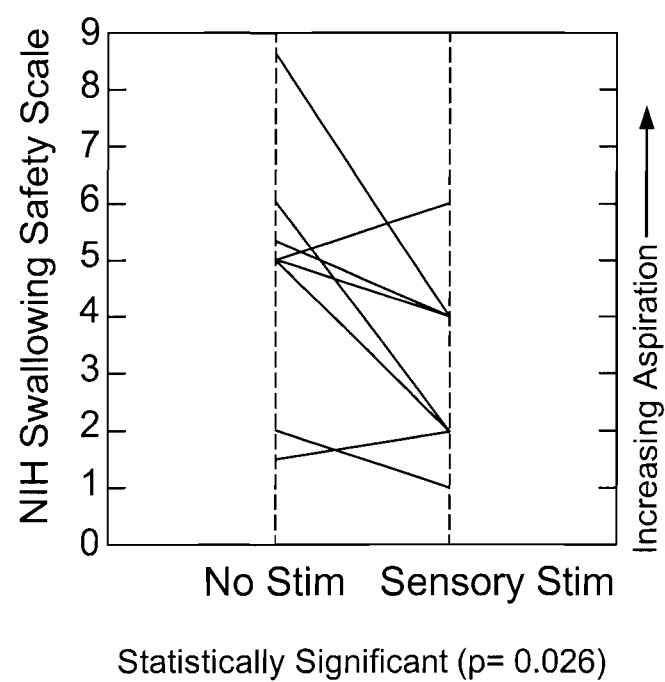
FIG. 3 is a graph of individual subject changes in aspiration seen in comparison with swallowing without stimulation versus swallowing with low levels of electrical stimulation at about 2 mA applied at the top the throat on the NIH swallowing safety scale.

Providing low levels of sensory stimulation to the throat significantly reduces the risk of aspiration in patients with severe swallowing disorders. FIG. 3 depicts individual subject reductions in aspiration on the NIH swallowing safety scale seen in comparison with swallowing without stimulation versus swallowing with low levels of electrical stimulation at about 2 mA applied on the throat.

Figure 4:
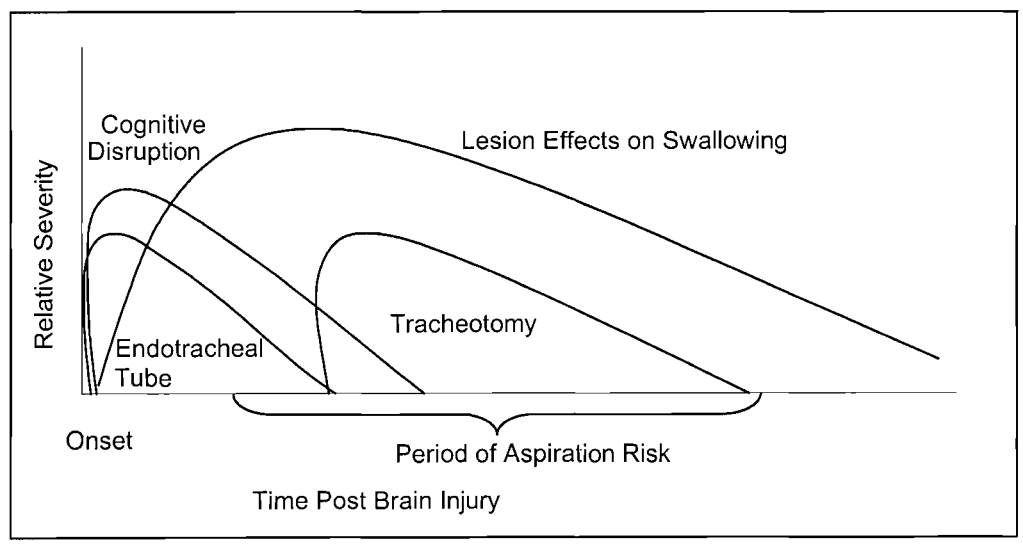
FIG. 4 is a graph depicting conceptualization of events post brain injury, placing patients at high risk of aspiration post extubation with tracheotomy due to reduced afferent stimulation in the upper airway and restricted oral intake, limiting return of reflexive swallowing.

FIG. 4 illustrates the events with relative severity and duration after the onset of brain injury. Following loss of consciousness due to brain injury or stroke or following coronary artery bypass graft, many subjects are intubated to maintain the airway for ventilation. As they recover cognitive function, extubation of the endrotracheal tube occurs. At this point it has been found that the swallowing reflex is reduced. There are most likely several factors contributing to this. First, sensory feedback 201 from the upper airway to the brain is reduced due to changes in the sensory function of the mucosa in the upper airway possibly as a result of injury to the mucosa by the endrotracheal tube, and sensory organs of nerve endings supplying those organs due to the pressure of the endrotracheal tube on the mucosa or resultant edema in the upper airway. In some subjects tissue granulation/ulceration occurs when the endrotracheal tube has been in place for prolonged periods (over one week). Upon extubation such subjects often receive a tracheotomy to provide an adequate airway. It has been shown that during this period following intubation that the normal swallowing reflex is reduced in patients increasing their risk of aspiration of their own saliva. In addition to loss of the swallowing reflex, when such subjects have a tracheotomy, their sensory input to the upper airway is further reduced because of a lack of air flow through the hypopharynx. In addition, such subjects are often placed on a restricted oral intake to prevent aspiration. As a result of their, "nothing per oral" (NPO) status, such subjects are not swallowing and may be fed through a nasogastnc tube or long-term by enteric means for several days or weeks. All of these factors reduce reflexive swallowing.

Figure 5:
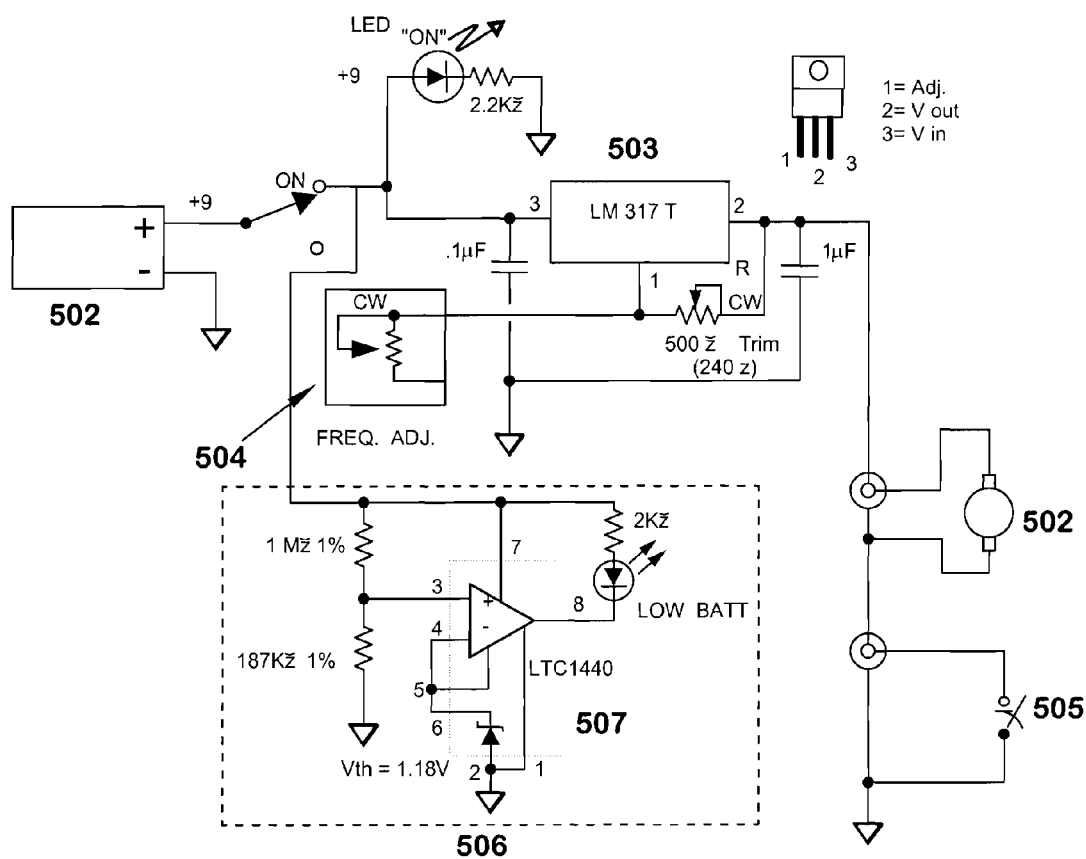
FIG. 5 is a diagram of the design of the circuitry for the throat vibrator component of the device.

In FIG. 5, the vibro-tactile stimulator is a battery-powered unit that controls a small DC motor 501. The current from a single 9 Volt transistor battery 502 is controlled by an LM317 (National Semiconductor Corporation), 3-terminal adjustable regulator 503 used as a current source. An internal adjustable potentiometer 504 allows the subject to preset the output current (measured as a voltage) of the regulator 503, which, in turn, will set the vibration frequency of the motor 501.

It has been suggested from animal data that a vibrating frequency of 20 to 30 Hz in the canine and 70 to 80 in the rabbit is particularly effective in eliciting the swallowing reflex. To generate this low frequency vibration required finding a small, low voltage DC motor (10 mm dia×25.4 mm in length) with a planetary gearbox (Faulhaber, Model 1016M). The gearbox reduces the output RPM to the desired range and increases the available torque. An eccentrically loaded mass (machined brass, currently 3.3 grams) is attached to the output shaft to generate the vibration. The mass weight can be changed to increase or decrease the vibration amplitude. A lightweight, sealed aluminum tube encapsulates the motor and mass assembly and is attached with thin, hook-and-loop fastening strips to an elastic wrap that can be positioned over the desired area of the throat.

The subject controls the stimulator circuit by pressing an external pushbutton "ON" switch 505. Pressing the switch will also activate an LED "ON" indicator light. When the button is released, the vibration pulses stop. There is no delay between pressing the "ON" switch and the vibration to the throat area.

A low battery indicator 506 is included using an LTC 1440 (Linear Technology) comparator 507 used as a battery system monitor. When the battery voltage drops below 7.6 Volts, an LED "Low Battery" indicator comes on.

Figure 6:
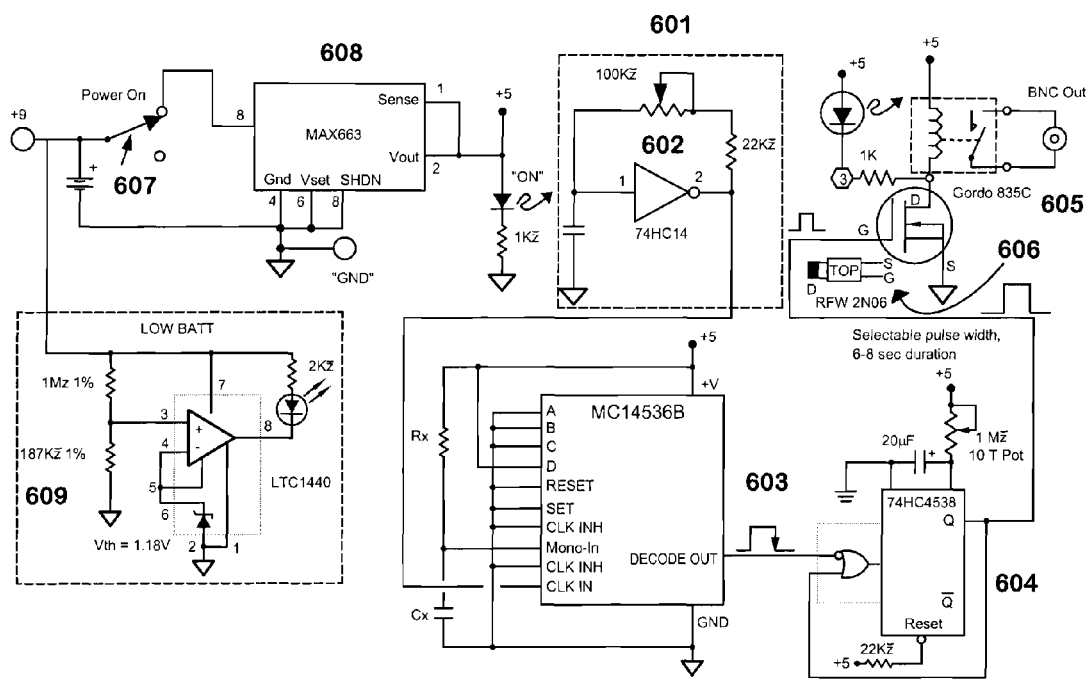
FIG. 6 is a diagram of the design of the circuitry for the automatic timer component of the device.

In FIG. 6, an additional circuit is currently being constructed that will serve to automatically energize the Throat Vibrator Circuit at an adjustable time interval (currently between about 3 and about 6 minutes). By attaching this new device to the Switch Control connector, the vibrator motor will be automatically energized for the selected time period (currently, between about 6 and about 8 seconds). This automatic timing circuit will be used to train subjects to control their saliva when they are not eating.

The circuit in FIG. 6 incorporates a simple adjustable digital oscillator 601 using a 74HC14 (Motorola Hex Schmitt-Trigger Inverter) 602, which connects to a Motorola MC14536B Programmable Timer 603. The input clock frequency will determine when an output pulse is generated. The initial requirement is for an output pulse once about every 3 to 6 minutes. The output pulse from the timer 603 triggers an adjustable 74HC4538 (Motorola Dual Precision Monostable Multivibrator) 604. The output pulse width of this device sets the "On" time for the vibrator motor by energizing a reed relay (GORDO 835C) 605 through a FET switch (RFW 2N06) 606. An LED is illuminated when the vibrator motor relay switch is closed.

This timer unit is also powered with a 9 V. battery 607 regulated to +5 Volts using a (MAX663, Maxim/Dallas Semiconductor) 608. A low battery indicator 609 is also incorporated using the LTC1440 (Linear Technology) described in the Throat Vibrator Circuit description.

A subject can retrain their volitional motor control of swallowing by learning to press a button (or a switch) immediately before the onset of the pharyngeal phase of swallowing. A low level sensory stimulation to the throat area can substitute for a loss of oropharyngeal sensory triggering in enhancing a volitional elicitation of a swallow. By training the patient to provide this sensory stimulation immediately before a swallow, their volitional control can be enhanced along with the use of a substitute sensory stimulation.

Providing alternative sensory stimulation, preferably vibratory stimulation to the thyroid cartilage at about 40 to about 70 Hz, will enhance the triggering of the swallowing reflex in the brain. FIG. 7 is a histogram of the frequency of reports of urges to swallow at four different frequencies. FIG. 7 indicates a peak in the urge to swallow at about 59 Hz. Such alternative sensory stimulation can substitute for the normal sensory stimulation of the mucosa in the upper airway in eliciting the swallowing reflex in patients who no longer have a normal response to sensory stimulation of the mucosa in the upper airway.

Volitional motor control training with sensory stimulation to enhance the return of volitional swallowing can reduce the subject's risk as aspiration pneumonia and prevent serious illness and death in neurological diseases and disorders secondary to swallowing difficulties (dysphagia).

The present invention has been disclosed in connection with various embodiments and implementations. The present invention is not limited by these embodiments and implementations. The present invention is intended to be defined by the scope of the claims which follow and that such claims be interpreted as broadly as is reasonable.

What is claimed is:

1. An automatic stimulation controller device that cycles on and off to initiate and maintain vibro-tactile stimulation to induce swallowing during the day and/or night to provide saliva control by swallowing, the automatic stimulation controller device comprising:
a vibro-tactile stimulator configured to initiate vibro-tactile stimulation of a throat area of a subject;
an automatic timing circuit in communication with the vibro-tactile stimulator, the automatic timing circuit configured to initiate vibro-tactile stimulation of the throat area of the subject by the vibro-tactile stimulator at an adjustable time interval, the automatic timing circuit comprising:
an oscillator configured to output a clock signal;
a programmable timer configured to receive the clock signal and to generate a first output pulse responsive to the clock signal, wherein the clock signal is adjustable to control the adjustable time interval of between about 1 minute and about 5 minutes; and
an adjustable timer configured to provide a second output pulse responsive to the first output pulse of the programmable timer, the second output pulse configured to initiate the vibro-tactile stimulation, wherein the second output pulse is adjustable to allow for setting the duration of stimulation between about 1 second and about 10 seconds, wherein the automatic stimulation controller device is configured to be adjusted to different intervals and durations of stimulation, wherein the vibro-tactile stimulation is configured to be adjusted to stimulation rates of between about 40 Hz and about 70 Hz; and
a control mechanism configured to also cause the vibro-tactile stimulator to initiate the vibro-tactile stimulation upon volitional input from the subject, the control mechanism comprising a switch configured to enable the device to switch between an automatic mode utilizing the automatic timing circuit and a volitional mode utilizing the control mechanism.

2. The device of claim 1, wherein the device trains saliva control.

3. The device of claim 1, wherein the device is disableable during eating.

4. The device of claim 1, further comprising indicia of a state of the vibro-tactile stimulation.

5. The device of claim 4, wherein the indicia of the vibro-tactile stimulation comprises an illuminated light-emitting diode.

6. A stimulation controller device comprising:
a vibro-tactile stimulator configured to apply vibro-tactile stimulation to a throat area of a subject;
an oscillator configured to output a clock signal;
a programmable timer configured to receive the clock signal and to generate a first output pulse responsive to the clock signal, wherein the clock signal is adjustable to control an adjustable interval of the vibro-tactile stimulation configured to be applied by the vibro-tactile stimulator to the throat area of the subject; and
an adjustable timer configured to provide a second output pulse responsive to the first output pulse of the programmable timer, the second output pulse configured to initiate the vibro-tactile stimulation of the subject; and
a control mechanism configured to also cause the vibro-tactile stimulator to apply the vibro-tactile stimulation upon volitional input from the subject, the control mechanism comprising a switch configured to enable the device to switch between an automatic mode utilizing the adjustable timer and a volitional mode utilizing the control mechanism,
wherein a width of the second output pulse is adjustable to allow for setting the duration of stimulation, and wherein the stimulation controller device is configurable to adjust to different intervals and durations of stimulation.

7. The device of claim 6, wherein the adjustable interval is between about 1 minute and about 5 minutes.

8. The device of claim 6, wherein the adjustable interval is between about 3 minutes and about 6 minutes.

9. The device of claim 6, wherein the duration of the vibro-tactile stimulation is between about 1 second and about 10 seconds.

10. The device of claim 6, wherein the duration of the vibro-tactile stimulation is between about 6 seconds and about 8 seconds.

11. The device of claim 6, wherein the vibro-tactile stimulator comprises a motor configured to perform the vibro-tactile stimulation for a duration determined by the second output pulse.

12. The device of claim 11, wherein the vibro-tactile stimulator has a frequency between about 40 Hz and about 70 Hz.

13. The device of claim 6, wherein a frequency of the vibro-tactile stimulator is adjustable.

14. The device of claim 6, wherein the device is configured to initiate the vibro-tactile stimulation during day.

15. The device of claim 6, wherein the device is configured to initiate the vibro-tactile stimulation during night.

16. The device of claim 6, wherein the device is configured to initiate the vibro-tactile stimulation during day or night.

17. The device of claim 6, wherein the device is configured to initiate the vibro-tactile stimulation during day and night.

18. The device of claim 6, wherein the vibro-tactile stimulation provides saliva control.

19. The device of claim 6, wherein inducing the vibro-tactile stimulation trains saliva control.

20. The device of claim 6, wherein the device is disableable during eating.

21. The device of claim 6, further comprising indicia of the vibro-tactile stimulation.

22. The device of claim 21, wherein the indicia of the vibro-tactile stimulation comprises an illuminated light.

23. The device of claim 11, further comprising a control mechanism configured to adjust a voltage applied to the motor and thereby adjust the stimulation rate of the device.

24. The device of claim 23, wherein the control mechanism comprises a potentiometer.

25. A stimulation controller device comprising:
a vibro-tactile stimulator configured to apply vibro-tactile stimulation to a throat area of a subject;
an oscillator configured to output a clock signal;
a programmable timer configured to receive the clock signal and to generate a first output pulse responsive to the clock signal, wherein the clock signal is adjustable to control an adjustable interval of the vibro-tactile stimulation to induce swallowing in the subject; and
an adjustable timer configured to provide a second output pulse responsive to the first output pulse of the programmable timer, the second output pulse configured to initiate the vibro-tactile stimulation of the subject; and
a control mechanism configured to also cause the vibro-tactile stimulator to apply the vibro-tactile stimulation upon volitional input from the subject, the control mechanism configured to enable the device to switch between an automatic mode utilizing at least the adjustable timer and a volitional mode utilizing the control mechanism,
wherein the second output pulse is adjustable to allow for setting the duration of stimulation, and wherein the stimulation controller device is configurable to adjust to different rates and durations of stimulation.

26. The device of claim 25, wherein the adjustable interval is between about 1 minute and about 5 minutes.

27. The device of claim 25, wherein the adjustable interval is between about 3 minutes and about 6 minutes.

28. The device of claim 25, wherein the duration of the vibro-tactile stimulation is between about 1 second and about 10 seconds.

29. The device of claim 25, wherein the duration of the vibro-tactile stimulation is between about 6 seconds and about 8 seconds.

30. The device of claim 25, wherein the vibro-tactile stimulator comprises a motor configured to perform the vibro-tactile stimulation responsive to the second output pulse.

31. The device of claim 30, wherein a frequency of the vibro-tactile stimulator is adjustable.

32. The device of claim 30, wherein the vibro-tactile stimulator has a frequency between about 40 Hz and about 70 Hz.

33. The device of claim 25, wherein the device is configured to initiate the vibro-tactile stimulation during day.

34. The device of claim 25, wherein the device is configured to initiate the vibro-tactile stimulation during night.

35. The device of claim 25, wherein the device is configured to initiate the vibro-tactile stimulation during day or night.

36. The device of claim 25, wherein the device is configured to initiate the vibro-tactile stimulation during day and night.

37. The device of claim 25, further comprising indicia of the vibro-tactile stimulation.

38. The device of claim 37, wherein the indicia of the vibro-tactile stimulation comprises an illuminated light-emitting diode.

39. The device of claim 25, wherein the vibro-tactile stimulation is configured to induce swallowing to train the subject to control saliva when not eating.

40. The device of claim 25, wherein the vibro-tactile stimulation is configured to reduce stuttering.

41. The device of claim 25, wherein the vibro-tactile stimulation is configured to treat spasmodic dysphonia.

* * * * *